United States Patent
Karim et al.

(10) Patent No.: US 9,409,840 B2
(45) Date of Patent: Aug. 9, 2016

(54) CARBON SUPPORTED COBALT AND MOLYBDENUM CATALYST AND USE THEREOF FOR PRODUCING LOWER ALCOHOLS

(75) Inventors: Khalid Karim, Riyadh (SA); Asad Khan, Riyadh (SA)

(73) Assignee: Saudi Basic Industries Corporation, Riyadh (SA)

(*) Notice: Subject to any disclaimer, the term of this patent is extended or adjusted under 35 U.S.C. 154(b) by 0 days.

(21) Appl. No.: 14/122,181

(22) PCT Filed: Jun. 28, 2012

(86) PCT No.: PCT/EP2012/002711
§ 371 (c)(1),
(2), (4) Date: Feb. 4, 2014

(87) PCT Pub. No.: WO2013/007345
PCT Pub. Date: Jan. 17, 2013

(65) Prior Publication Data
US 2014/0142206 A1    May 22, 2014

(30) Foreign Application Priority Data
Jul. 8, 2011  (EP) ..................................... 11075164

(51) Int. Cl.
| | | |
|---|---|---|
| B01J 21/18 | (2006.01) | |
| C07C 29/157 | (2006.01) | |
| B01J 23/882 | (2006.01) | |
| B01J 23/887 | (2006.01) | |
| C07C 29/156 | (2006.01) | |
| B01J 37/03 | (2006.01) | |

(52) U.S. Cl.
CPC .............. *C07C 29/157* (2013.01); *B01J 21/18* (2013.01); *B01J 23/882* (2013.01); *B01J 23/8872* (2013.01); *B01J 37/033* (2013.01); *B01J 37/035* (2013.01); *C07C 29/156* (2013.01); *Y02P 20/52* (2015.11)

(58) Field of Classification Search
CPC ...... B01J 21/18; B01J 23/882; B01J 23/8872; B01J 29/156; B01J 37/035
USPC ........................................................ 502/185
See application file for complete search history.

(56) References Cited

U.S. PATENT DOCUMENTS

| | | | |
|---|---|---|---|
| 4,177,203 A | 12/1979 | Kolbel et al. | |
| 4,752,622 A | 6/1988 | Stevens | |
| 4,882,360 A | 11/1989 | Stevens | |
| 5,780,381 A | 7/1998 | Wilson et al. | |
| 7,375,055 B2 | 5/2008 | Van Berge et al. | |
| 7,396,798 B2 | 7/2008 | Ma et al. | |
| 2008/0280754 A1* | 11/2008 | Toledo Antonio | ....... B01J 23/85 502/177 |
| 2014/0135411 A1 | 5/2014 | Karim et al. | |

FOREIGN PATENT DOCUMENTS

| | | |
|---|---|---|
| CN | 1631527 A | 6/2005 |
| CN | 101664682 A | 3/2010 |
| CN | 101733135 A | 6/2010 |
| EP | 0119609 A1 | 9/1984 |
| EP | 0172431 A2 | 2/1986 |
| JP | H05-135772 A | 6/1993 |
| JP | 2011-029171 A | 2/2011 |
| WO | WO-03/041860 A2 | 5/2003 |
| WO | WO-03/076074 A1 | 9/2003 |
| WO | WO-2009/032982 A2 | 3/2009 |
| WO | WO-2010/02618 A1 | 1/2010 |
| WO | WO-2010/098668 A2 | 9/2010 |
| WO | WO-2011/003884 A1 | 1/2011 |
| WO | WO 2012/078277 * | 6/2012 |
| WO | WO-2012/143131 A1 | 10/2012 |
| WO | WO-2013/007345 A1 | 1/2013 |

OTHER PUBLICATIONS

International Preliminary Report on Patentability issued by the International Bureau on Oct. 22, 2013 for PCT/EP2012/001699 filed Apr. 19, 2012 and published as WO 2012/143131 on Oct. 26, 2012 (Applicants—Saudi Basic Industries Corporation, et al.; Inventors—Karim, et al.) (5 pages).

International Search Report mailed by the International Bureau on Jul. 17, 2013 for PCT/EP2012/001699 filed Apr. 19, 2012 and published as WO 2012/143131 on Oct. 26, 2012 (Applicants—Saudi Basic Industries Corporation, et al.; Inventors—Karim, et al.) (2 pages).

Written Opinion mailed by the International Bureau on Jul. 17, 2013 for PCT/EP2012/001699 filed Apr. 19, 2012 and published as WO 2012/143131 on Oct. 26, 2012 (Applicants—Saudi Basic Industries Corporation, et al.; Inventors—Karim, et al.) (4 pages).

Preliminary Amendment filed Sep. 19, 2013 for U.S. Appl. No. 14/006,199, filed Jan. 31, 2014 and published as U.S. 2014/0135411 on May 15, 2014 (Applicants—Saudi Basic Industries Corporation, et al.; Inventors—Karim, et al.) (3 pages).

Preliminary Amendment filed Nov. 25, 2013 for U.S. Appl. No. 14/006,199, filed Jan. 31, 2014 and published as U.S. 2014/0135411 on May 15, 2014 (Applicants—Saudi Basic Industries Corporation, et al.; Inventors—Karim, et al.) (5 pages).

Auer (1998) Carbons as supports for industrial precious metal catalysts. Applied Catalysis A: General, 173: 259-271.

Bao J, et al. (2003) A highly active K-Co-Mo/C catalyst for mixed alcohol synthesis from Co + H2. Chemical Communications, 9(6): 746-747.

Commereuc (1980) Catalytic synthesis of low molecular weight olefins from CO; and H2 with Fe (CO)5, FE3(CO)12, and [HFe3(CO)11]—supported on inorganic oxides. J. Chem. Soc., Chem. Commun.: 154-155.

Dry (2004) Chapter 3—Chemical concepts used for engineering purposes. Stud. Surf. Sci. Catal, 152: 196-257.

(Continued)

*Primary Examiner* — Jafar Parsa
(74) *Attorney, Agent, or Firm* — Ballard Spahr LLP

(57) ABSTRACT

The present invention relates to a method for preparing a catalyst composition comprising cobalt and molybdenum on a carbon support, characterized in that the cobalt- and molybdenum-source are dissolved in an organic solvent that is miscible with water. Moreover, a carbon supported cobalt molybdenum catalyst composition obtainable by said method and a process for producing alcohols from syngas using said carbon supported cobalt molybdenum catalyst composition is provided.

9 Claims, No Drawings

(56) References Cited

OTHER PUBLICATIONS

Fujimoto K, et al. (1985) Synthesis of C1-C7 alcohols from synthesis gas with supported cobalt catalysts. Applied Catalysis, 13(2): 289-293.

Li X, et al. (1998) Higher alcohols from synthesis gas using carbon-supported doped molybdenum-based cataylsts. Industrial Engineering Chemistry Research, 37(10): 3853-3863.

Mirzaei, et al. (2009) Fischer-Tropsch Synthesis over Iron Manganese Catalysts: Effect of Preparation and Operating Conditions on Catalyst Performance. Adv. Phys. Chem, 2009: 1-12.

Okuhara (1981) Synthesis of light olefins from CO and H2 over highly dispersed Ru/K-Al2O3 derived from Ru3(CO)12. J. Chem. Soc., Chem. Commun., 1981(21): 1114-1115.

International Preliminary Report on Patentability issued by the International Bureau on Jan. 14, 2014 for PCT/EP2012/002711 filed on Jun. 28, 2012 and published as Wo 2013/007345 on Jan. 17, 2013 (Applicants—Saudi Basic Industries Corporation, et al.; Inventors—Karim, et al.) (7 pages).

International Search Report mailed by the International Bureau on Oct. 31, 2012 for PCT/EP2012/002711 filed on Jun. 28, 2012 and published as WO 2013/007345 on Jan. 17, 2013 (Applicants—Saudi Basic Industries Corporation, et al.; Inventors—Karim, et al.) (4 pages).

Written Opinion mailed by the International Bureau on Oct. 31, 2012 for PCT/EP2012/002711 filed on Jun. 28, 2012 and published as WO 2013/007345 on Jan. 17, 2013 (Applicants—Saudi Basic Industries Corporation, et al.; Inventors—Karim, et al.) (6 pages).

Extended European Search Report issued on Dec. 23, 2011 for EP 11075164.1 (Applicants—Saudi Basic Industries Corporation, et al.; Inventors—Karim, et al.) (7 pages).

Knuniants, et al., Soviet Chemical Encyclopedia, vol. 2, (1990) (pp. 338-339).

Matos, et al., "Activated carbon supported Ni-Mo: effects of pretreatment and composition on catalyst reducibility and on ethylene conversion", Applied Catalysis A: General 152 (1997) (pp. 27-42).

* cited by examiner

CARBON SUPPORTED COBALT AND MOLYBDENUM CATALYST AND USE THEREOF FOR PRODUCING LOWER ALCOHOLS

CROSS-REFERENCE TO RELATED APPLICATIONS

This application is a National Phase Application of International Application No. PCT/EP2012/002711, filed Jun. 28, 2012, which claims priority to European Patent Application No. 11075164.1, filed Jul. 8, 2011, all of which are incorporated herein fully by this reference.

The present invention relates to a method for preparing a catalyst composition comprising cobalt and molybdenum on a carbon support, characterized in that the cobalt- and molybdenum-source are dissolved in an organic solvent that is miscible with water. Moreover, a carbon supported cobalt molybdenum catalyst composition obtainable by said method and a process for producing alcohols from syngas using said carbon supported cobalt molybdenum catalyst composition is provided.

Gaseous mixtures comprising hydrogen ($H_2$) and carbon monoxide (CO) can be converted into a hydrocarbon product stream by a catalytic process known as Fischer-Tropsch synthesis (F-T synthesis). The most common catalysts useful in F-T synthesis ("F-T catalysts") are based on Fe and/or Co, although Ni- and Ru-based catalysts have also been described (see e.g. U.S. Pat. No. 4,177,203; Commereuc (1980) J. Chem. Soc., Chem. Commun. 154-155; Okuhara (1981) J. Chem. Soc., Chem. Commun. 1114-1115). Generally, Ni-based catalysts are relatively more selective for producing methane whereas Co-, Fe- and Ru-based catalysts are more selective for hydrocarbons having at least two carbon atoms (C2+ hydrocarbons). Moreover, the selectivity for C2+ hydrocarbons can be increased by decreasing the $H_2$:CO ratio, decreasing the reaction temperature and decreasing the reactor pressure.

It has been previously described that alcohols may be produced by F-T synthesis using a catalyst composition having as a first component molybdenum in free or combined form, as a second component a promoter of an alkali or alkaline earth element in free or combined form and as a third component cobalt in free or combined form (see EP 0 172 431 A2). Preferably, the first and third component is present as the sulphide. The catalyst of EP 0 172 431 A2 may further comprise a support, wherein carbon supports are preferred.

A major drawback of conventional catalysts for producing alcohols by F-T synthesis is that the selectivity of the process for alcohols is relatively low, resulting in a relatively low yield of alcohols.

It was an object of the present invention to provide an improved catalyst suitable for producing alcohols from a syngas mixture comprising hydrogen and carbon monoxide.

The solution to the above problem is achieved by providing the embodiments as described herein below and as characterized in the claims. Accordingly, the present invention provides a method for preparing a catalyst composition comprising cobalt (Co) and molybdenum (Mo) on an activated carbon support comprising the steps:

(a) dissolving a soluble cobalt-comprising compound and a soluble molybdenum-compound in one or more organic solvents that are miscible with water to form a cobalt- and molybdenum-comprising solution;

(b) admixing an aqueous alkaline solution to the cobalt- and molybdenum-comprising solution in the presence of activated carbon support to precipitate insoluble cobalt- and molybdenum-comprising compound on activated carbon support to form a solid catalyst precursor; and (c) separating the solid catalyst precursor from the liquids, washing and drying the solid catalyst precursor and calcining the solid catalyst precursor in an inert atmosphere.

In the context of the present invention, it was surprisingly found that the catalyst produced by the method of the present invention has a significantly increased selectivity for C2 and C3 alcohols (alcohols having 2 or 3 carbon atoms), while maintaining a good conversion, when compared to a conventional carbon supported cobalt molybdenum catalyst or when compared to a carbon supported cobalt molybdenum catalyst wherein the soluble cobalt-comprising compound and the soluble molybdenum-compound are dissolved in water. Accordingly, the catalyst for converting syngas to C2 and C3 alcohols provided by the present invention is characterized in that it allows a superior C2 and C3 alcohol yield. In addition thereto, a decrease in $CO_2$ formation could be observed, which is an undesired side-product produced in F-T synthesis.

In the cobalt-molybdenum-solution preparation step (a) as described herein, a solution comprising soluble cobalt- and molybdenum-comprising salts may be prepared in any organic solvent that is miscible with water or a mixture of any organic solvents that are miscible with water. Suitable solvents are all compounds in which the chosen salts are soluble and which are easy to remove again in the separation step as defined herein. Generally, solvents having a dielectric constant of 15 of more are miscible with water (polar solvents). Preferably, the solvent is a polar protic solvent. Examples of suitable solvents include, but are not limited to, methanol, ethanol, 1-butanol, propanol, pentanol, hexanol, ethylene glycol and glycerol. Preferably, the solvent is selected from the group consisting of alcohols comprising 1-3 carbon atoms (C1-C3 alcohols). Most preferably, the solvent is ethanol. The solvent and the obtained solution may be heated to facilitate dissolving of the cobalt- and molybdenum-comprising salts. Preferably, the solvent and the obtained solution is heated to at least about 60° C. and up to about 95° C. (about 60-95° C.), most preferably to about 75-85° C. Heating the solvent to a temperature above its boiling point is to be avoided.

In one embodiment, the cobalt- and molybdenum-comprising solution is formed in step (a) by separately dissolving the soluble cobalt-comprising compound and the soluble molybdenum-comprising compound in one or more organic solvents that are miscible with water followed by admixing the cobalt-comprising solution and the molybdenum-comprising solution. The organic solvent that is miscible with water wherein the cobalt-comprising compound is dissolved and the organic solvent that is miscible with water wherein the molybdenum-comprising compound is dissolved may be the same one or more solvents that are miscible with water or may be different solvents that are miscible with water.

Any source of cobalt or molybdenum that is soluble in the selected solvent may be used to prepare the cobalt- and molybdenum-comprising solution. Suitable cobalt- and molybdenum sources may be in the form of nitrate, chloride, carbonate, bicarbonate, and oxide. A particularly suitable soluble cobalt-comprising compound is cobalt acetate $Co(CH_3CO_2)_2$ and a particularly suitable molybdenum-comprising compound is ammonium heptamolybdate $(NH_4)_6Mo_7O_{24}$.

In the catalyst precursor forming step (b) as described herein, a precipitate is formed by converting the soluble cobalt- and molybdenum-comprising salts into insoluble compounds by admixing an alkaline solution as precipitant, preferably under constant agitation. Preferably, the alkaline solution is selected from the group consisting of aqueous ammonia, sodium carbonate, ammonium bicarbonate and ammonium carbonate. Most preferably, the precipitate is formed by mixing a suitable amount of aqueous ammonia to a cobalt-molybdenum-solution. The amount of alkaline compound present in the alkaline solution is selected so that it is at least sufficient for the stoichiometric reaction with the soluble cobalt- and molybdenum-comprising salts present. Preferably, the amount of alkaline compound present in the alkaline solution is 1-10 times the stoichiometric required amount. Preferably, the ammonium hydroxide is heated to the same temperature as the cobalt-molybdenum-solution. The pH at the end of the precipitation step preferably is at least 8, more preferably at least 9. The temperature of the mixture may be kept constant until the precipitate is formed, preferably under constant agitation. The pH difference and concentration of the precipitant was found to affect the morphology of catalyst material.

In the catalyst precursor forming step, the aqueous alkaline solution is admixed to the cobalt- and molybdenum-comprising solution in the presence of activated carbon support material. Preferably, the activated carbon support material has a specific surface area of about 800-1200 $m^2/g$, and most preferably of about 850-950 $m^2/g$. Carbon catalyst supports are very well known in the art and may be prepared from coals and coal-like materials, petroleum-derived carbons and plant-derived carbons (see Auer (1998) Applied Catal 259-271). Any commercially available activated carbon source may be used. Preferably, the activated carbon is derived from group consisting of coconut shell, peat, wood and synthetic carbon nano tube (see U.S. Pat. No. 7,396,798). Most preferably, the carbon support is coconut shell carbon having a specific surface area of about 800-900 $m^2/g$.

In step (c) as described herein, the solid catalyst precursor (i.e. the solid phase of the mixture that is formed after completing the catalyst precursor forming step (b)) is separated from the liquid (i.e. the liquid phase of the mixture that is formed after completing the precipitate forming step (b)) using any conventional method which allows the separation of a precipitate from a liquid. Suitable methods include, but are not limited to, filtering, decanting and centrifugation. Subsequently the obtained solid may be washed, preferably using one of the solvents in which the solutions were made, more preferably with water, most preferably with distilled water. The solid then may be dried, preferably at about 110-120° C. for about 4-16 hours.

Subsequently, the obtained solid is calcined in an inert atmosphere to form a calcined catalyst. Preferably, the calcination is carried out at about 350-650° C. for about 3-8 hours. The skilled person is readily capable of selecting a suitable inert gas to form the inert atmosphere. Preferred inert gases are selected from the group consisting of helium, argon and nitrogen.

After calcination, the calcined catalyst may be formed into pellets using any conventional method. Said pellets may subsequently be sieved to obtain regularly sized particles. Said particles may be sized between about 0.65-0.85 mm.

In a further embodiment, the present invention provides the catalyst composition obtainable by the herein described method for preparing a catalyst composition comprising cobalt (Co) and molybdenum (Mo) on an activated carbon support. Accordingly, the present invention relates to a catalyst composition obtainable by the method comprising the steps:

(a) dissolving a soluble cobalt-comprising compound and a soluble molybdenum-compound in one or more organic solvents that are miscible with water to form a cobalt- and molybdenum-comprising solution;

(b) admixing an aqueous alkaline solution to the cobalt- and molybdenum-comprising solution in the presence of activated carbon support to precipitate insoluble cobalt- and molybdenum-comprising compound on activated carbon support to form a solid catalyst precursor; and (c) separating the solid catalyst precursor from the liquids, washing and drying the solid catalyst precursor and calcining the solid catalyst precursor in an inert atmosphere.

In a preferred embodiment, the catalyst composition obtained by the herein described method for preparing a catalyst composition comprising cobalt (Co) and molybdenum (Mo) on an activated carbon support is provided.

The catalyst composition of the present invention is readily distinguishable from previously described catalyst compositions by its composition and by its superior catalyst performance, such as the superior yield of C2 and C3 alcohols, when compared to a conventional carbon supported cobalt molybdenum catalyst or when compared to a carbon supported cobalt molybdenum catalyst wherein the soluble cobalt-comprising compound and the soluble molybdenum-compound are dissolved in water.

Accordingly, the present invention provides a catalyst composition for converting syngas to C2 and C3 alcohols comprising cobalt (Co) and molybdenum (Mo) on a carbon support (C) wherein the relative molar ratios of the elements comprised in said composition are represented by the formula:

$$Co_aMo_bC$$

wherein:
a is about 1E-3–0.3 and
b is about 1E-3–0.9;
and wherein the yield of C2 and C3 alcohols is more than 18, more preferably more than 20 and most preferably more than 25 mole-%.

Preferably, the Co and/or Mo comprised in the catalyst composition of the invention are not in sulphide form. This means that the catalyst composition of the present invention has not been sulphided with e.g. $H_2S$ as taught in EP 0 172 431 A2.

The amount of Co present in the catalyst composition is determined by the molar ratio of Co in relation to the carbon support C in the catalyst composition. The molar ratio of Co:C is about 1E-3–0.3:1 (also depicted as: $Co_aC$ wherein a is about 1E-3–0.3:1 or about 0.001–0.3:1). This means that the molar ratio of Co:C is between about 1E-3:1 (or about 0.001:1) and about 0.3:1. Most preferably, the molar ratio of Co:C is about 1E-2–0.3. It was found that when the catalyst composition comprises too much Co, the catalytic activity shifts towards hydrogenation which decreases catalyst selectivity for oxygenates and increases catalyst selectivity for non-oxygenated hydrocarbons.

The amount of Mo present in the catalyst composition is determined by the molar ratio of Mo in relation to the carbon support C in the catalyst composition. The molar ratio of Mo:C is about 1E-3–0.9:1 (also depicted as: $Mo_bC$ wherein b is about 1E-3–0.9:1 or about 0.001–0.9:1). This means that the molar ratio of Mo:C is between about 1E-3:1 (or about 0.001:1) and about 0.9:1. Most preferably, the molar ratio of Mo:C is about 5E-3–0.2. It was found that selectivity of the catalyst for $CO_2$ is increased when the catalyst composition comprises too much Mo. Moreover, it was found that the selectivity of the catalyst for oxygenates decreased when the catalyst comprises too little Mo.

Preferably, the molar ratio of Co:Mo is 1 or more. It was surprisingly found that catalyst selectivity for oxygenates is increased when the molar ratio of Co:Mo is 1 or more. More preferably, the molar ratio of Co:Mo is 1.2-4, even more preferably 1.5-3, particularly preferably 2-2.5 and most preferably about 2.2.

The catalyst composition of the present invention is preferably formed in regularly sized particles such as conventionally formed catalyst pellets and/or sieved catalyst particles. The catalyst composition of the present invention may comprise further components including but not limited to binders and lubricants. Any inert catalyst binder may be used. Preferably, the binder is selected from the group consisting of bentonite clay, colloidal silica and kaolin. Suitable lubricants are selected from the group consisting of hydrogenated cottonseed oil and hydrogenated soybeen oil.

Furthermore, the catalyst composition of the present invention may be diluted with an inert diluent. Suitable inert diluents are selected from the group consisting of silicon carbide, clay, alumina and silica. However, the skilled person is readily capable of selecting other suitable inert diluents.

In a further embodiment, the present invention relates to a process for producing a product stream comprising alcohols comprising contacting the catalyst composition as described herein with a gaseous mixture comprising hydrogen and carbon monoxide (syngas mixture). The product stream comprising alcohols is preferably produced by Fischer-Tropsch synthesis.

The terms "alcohols" is very well known in the art. Accordingly, an "alcohol" relates to any hydrocarbon compound in which a hydroxyl functional group (—OH) is bound to a carbon atom, usually connected to other carbon or hydrogen atoms. Preferred alcohols comprised in the product stream of the present process are C2-C3 alcohols, such as ethanol and propanol.

In the process of the present invention, the catalyst composition is preferably comprised in a fixed bed reactor; fluidized bed reactor; or a circulating bed reactor.

Preferably, the syngas mixture has a hydrogen ($H_2$) to carbon monoxide (CO) molar ratio of about 1-4 (i.e. $H_2$:CO is about 1:1 to about 1-4), preferably of about 1-2 and most preferably of about 1. The term "syngas mixture" as used herein relates to a gaseous mixture substantially consisting of hydrogen ($H_2$) to carbon monoxide (CO). The syngas mixture, which is used as a feed stream to the present process for producing alcohols, may comprise up to 10 mol-% of other components such as $CO_2$ and lower hydrocarbons (lower HC, such as methane). Said other components may be side-products or unconverted products obtained in the process used for producing the syngas mixture. Preferably, the syngas mixture comprises substantially no molecular oxygen ($O_2$). As used herein, the term "syngas mixture comprising substantially no $O_2$" relates to a syngas mixture which comprises such a low amount of $O_2$ so that the comprised $O_2$ does not interfere with the Fischer-Tropsch synthesis reaction. Preferably, the syngas mixture comprises not more than 1 mol-% $O_2$, more preferably not more than 0.5 mol-% $O_2$ and most preferably not more than 0.4 mol-% $O_2$.

The process conditions useful in the process of the present invention can be easily determined by the person skilled in the art; see Dry (2004) Stud. Surf. Sci. Catal 152:197-230 in "Fischer-Tropsch technology" eds. Steynberg and Dry. Accordingly, the Fischer-Tropsch synthesis is performed at a reaction temperature of about 150-450° C., preferably of about 150-350° C., a space velocity of about 400-5000 $h^{-1}$, preferably of about 2000 $h^{-1}$ and a pressure of between atmospheric and about 10 MPa, preferably a pressure of about 1-5 MPa. The catalyst may be stabilized for about 80-100 hours at about 150-350° C. before actual use.

In this respect, it should be noted that the reaction conditions have a marked effect on the catalytic performance. It has been reported that selectivity on a carbon basis is essentially a function of the probability of chain growth, α; see Dry (2004) loc. cit. Control of the product selectivity is to a large extent determined by the factors that influence the value of α. The main factors are the temperature of the reaction, the gas composition and more specifically the partial pressures of the various gases in contact with catalyst inside the reactor. Overall, by manipulating these factors a high degree of flexibility can be obtained regarding the type of product and the carbon range. An increase in FT-synthesis operating temperature shifts the selectivity profile to lower carbon number products. Desorption of growing surface species is one of the main chain termination steps and since desorption is an endothermic process so a higher temperature should increase the rate of desorption which will result in a shift to lower molecular mass products. Similarly, the higher the CO partial pressure the more is the catalyst surface covered by adsorbed monomers. The lower the coverage by partially hydrogenated CO monomers the higher the probability of chain growth is expected to be; see also Mirzaei et al., Adv. Phys. Chem., 2009, 1-12. Accordingly, the two key steps leading to chain termination are desorption of the chains yielding unsaturated hydrocarbons and hydrogenation of the chains to yield saturated hydrocarbons.

In a further embodiment, the present invention relates to a process for producing a product stream comprising alcohols comprising the method for preparing the catalyst composition as described herein and contacting the obtained catalyst composition with a syngas mixture. Accordingly, the present invention provides a process for producing a product stream comprising alcohols, preferably by Fischer-Tropsch synthesis, comprising the steps:

(a) dissolving a soluble cobalt-comprising compound and a soluble molybdenum-compound in one or more organic solvents that are miscible with water to form a cobalt- and molybdenum-comprising solution;

(b) admixing an aqueous alkaline solution to the cobalt- and molybdenum-comprising solution in the presence of activated carbon support to precipitate insoluble cobalt- and molybdenum-comprising compound on activated carbon support to form a solid catalyst precursor; and (c) separating the solid catalyst precursor from the liquids, washing and drying the solid catalyst precursor and calcining the solid catalyst precursor in an inert atmosphere.

The present invention will now be more fully described by the following non-limiting Examples.

EXAMPLE 1 (COMPARATIVE)

$CoMoS_2$

A co-precipitated cobalt/molybdenum sulfide is prepared with a Mo/Co atomic ratio of about 2:1. Fifteen grams of $(NH_4)_6Mo_7O_{24}.4H_2O$ (0.085 Moles Mo) is dissolved in 106 $cm^3$ of 22% $(NH_4)_2S$ in water and stirred at 60° C. for one hour to form $(NH_4)_2MoS_4$. A solution of 10.5 grams of $Co(CH_3CO_2)_2$ (0.042 moles Co) in 200 $cm^3$ of water was prepared. The two solutions were then added simultaneously, drop wise to a stirred solution of 30% aqueous acetic acid in a baffled flask at 50° C. over a one hour period. After stirring for an additional hour the reaction mixture is filtered and the filter cake dried at room temperature and then calcined for one hour at 500° C. in an inert atmosphere such as nitrogen. The calcined Co/Mo Sulfide is ground together with 2.0 g of bentonite clay, 1.0 g of $K_2CO_3$ and 0.4 g of sterotex lubricant in a mortar and pestles and used for catalyst testing.

EXAMPLE 2 (COMPARATIVE)

100 ml each of Co and Mo solutions was prepared by dissolving 10.5 g of cobalt acetate $[Co(CH_3CO_2)_2]$ and 15 g of ammonium molybdate tetrahydrate $[(NH_4)_6Mo_7O_{24}.4H_2O]$ in distilled water. Both solutions were premixed and heated to 80° C. The $NH_3$ precipitating solution (200 ml of 5.6M $NH_3$ solution) was also preheated to 80° C. 6.4 g of activated carbon (derived from coconut shell) was added into 100 ml of distilled water in the precipitation vessel. Both reagents (mixed metal salts solutions and $NH_3$ solution) were combined together in the reaction vessel at 80° C. at a combined pumping rate of 6.7 ml/min (3.3 ml/min $NH_3$ solution, 3.3 ml/min metals solution). The reagents were combined in the reaction vessel (80° C.) containing activated carbon in 100 ml of water. The pH was varied from 4.35-9.00. The duration of reaction was ca. 1 h. This solution was immediately filtered through a preheated funnel and washed (using 500 ml of warm distilled water). The precipitates were dried at 110° C. for 16 h followed by calcinations at 500° C. under continuous flow of helium for 24 h.

EXAMPLE 3

100 ml each of Co and Mo solutions was prepared by dissolving 10.5 g of cobalt acetate $[Co(CH_3CO_2)_2]$ and 15 g of ammonium molybdate tetrahydrate $[(NH_4)_6Mo_7O_{24}.4H_2O]$ in glycerol. Both solutions were premixed and heated to 80° C. The $NH_3$ precipitating solution (200 ml of 5.6M $NH_3$ solution) was also preheated to 80° C. 6.4 g of activated carbon (derived from coconut shell) was added into 100 ml of glycerol in the precipitation vessel. Both reagents (mixed metal salts solutions and $NH_3$ solution) were combined together in the reaction vessel at 80° C. at a combined pumping rate of 6.7 ml/min (3.3 ml/min $NH_3$ solution, 3.3 ml/min metals solution). The reagents were combined in the reaction vessel (80° C.) containing activated carbon in 100 ml of glycerol. The pH was varied from 4.35-9.00. The duration of reaction was ca. 1.5 h. This solution was immediately filtered through a preheated funnel and washed (using 500 ml of warm distilled water). The precipitates were dried at 110° C. for 16 h followed by calcinations at 500° C. under continuous flow of helium for 24 h.

EXAMPLE 4

100 ml each of Co and Mo solutions was prepared by dissolving 10.5 g of cobalt acetate $[Co(CH_3CO_2)_2]$ and 15 g of ammonium molybdate tetrahydrate $[(NH_4)_6Mo_7O_{24}.4H_2O]$ in pure ethanol. Both solutions were premixed and heated to 70 to 75° C. The $NH_3$ precipitating solution (200 ml of 5.6M $NH_3$ solution) was also preheated to 80° C. 6.4 g of activated carbon (derived from coconut shell) was added into 100 ml of glycerol in the precipitation vessel. Both reagents (mixed metal salts solutions and $NH_3$ solution) were combined together in the reaction vessel at 80° C. at a combined pumping rate of 6.7 ml/min (3.3 ml/min $NH_3$ solution, 3.3 ml/min metals solution). The reagents were combined in the reaction vessel (80° C.) containing activated carbon in 100 ml of ethanol. The pH was varied from 4.35-9.00. The duration of reaction was ca. 1.5 h. This solution was immediately filtered through a preheated funnel and washed (using 500 ml of warm distilled water). The precipitates were dried at 110° C. for 16 h followed by calcinations at 500° C. under continuous flow of helium for 24 h.

Catalyst Testing

Catalytic tests were carried out using fixed bed micro reactor. The dilution of catalyst was performed by intimate mixing of the catalyst with silicon carbide (4.8 ml/5.2 ml catalyst). Prior to the catalytic run, system leakage test was carried out using nitrogen (Oxygen free, BOC). After the system was found safe and leak-free, syngas was gradually introduced to the system, replacing the nitrogen. The composition of the feedstream was $CO:H_2:N_2=47.5:47.5:5$. Accordingly, the feedstream comprised syngas having $CO:H_2$ molar ratio of 1. Following the complete replacement, the system was brought up to the required pressure, followed by heating with a ramping rate of 1 K/min until it reached the desired temperature. All catalysts were studied under identical reaction conditions. Reaction pressure was 7.5 MPa and temperature of reaction was 250° C.

Analysis of gaseous product was achieved by an online gas chromatograph (GC, Varian 3800). A 5 m*⅛ inch stainless steel Porapak-Q column (mesh size 80-100) was used to separate the reactants and products. Concentrations of hydrogen, carbon monoxide, carbon dioxide and nitrogen were analyzed by a thermal conductivity detector (TCD). The TCD compares the conductivity of the analyzed gas to that of a reference gas. Conversion was determined using an internal standard, nitrogen. Organic compounds such as hydrocarbons and oxygenates were determined by a flame ionization detector (FID). By using a hydrogen and air flame, the FID burns the organic compounds into ions whose amounts are roughly proportional to the number of carbon atoms present. Liquid products from alcohols reactor were collected and identified by gas chromatography mass spectrometer (GC-MS, Perkin Elmer TurboMass). Quantification of liquid products was determined by an offline GC equipped with a Chrompack capillary column (CP-Sil 8CB, 30 m, 0.32 mm, 1 μm) and an FID detector.

The provided values have been calculated as follows:
Conversion:

An indication of the activity of the catalyst was determined by the extent of conversion of the carbon monoxide or for more active catalysts by the extent of volume reduction of the reagent gases (using nitrogen as internal standard). The basic equation used was:

$$\text{Conversion \%} = \text{Moles of } CO_{in} - \text{moles of } CO_{out}/\text{moles of } CO_{in} * 100/1$$

Selectivity

First of all, the varying response of the detector to each product component was converted into % v/v by, multiplying them with online calibration factors. Then these were converted into moles by taking account the flow out of internal standard, moles of feed in and time in hours. Moles of each product were converted into mole-% and selectivity-% was measured by taking carbon numbers into account.

TABLE 1

| Example | 1 | 2 | 3 | 4 |
|---|---|---|---|---|
| Catalyst | $CoMoS_2$ | $Co_{0.126}Mo_{0.255}C$ | $Co_{0.126}Mo_{0.255}C$ | $Co_{0.126}Mo_{0.255}C$ |
| Co/Mo/C (wt-%) | | 25/11.6/63.4 | 25/11.6/63.4 | 25/11.6/63.4 |
| solvent | water | water | glycerol | ethanol |
| Precipitant conc. (M) | — | 5.6 | 5.6 | 5.6 |

TABLE 1-continued

| Example | 1 | 2 | 3 | 4 |
|---|---|---|---|---|
| $H_2$:CO | 1 | 1 | 1 | 1 |
| CO conversion (mole-%) | 41 | 28 | 35 | 42 |
| $CO_2$ selectivity | 25.4 | 3.8 | 3 | 1.7 |
| $CH_4$ selectivity | 9.19 | 1.27 | 2.5 | 14.97 |
| $C_2$-$C_6$ selectivity | 2.68 | 1 | 3.8 | 1.60 |
| Methanol selectivity | 10.6 | 26.21 | 24.1 | 18.44 |
| Ethanol selectivity | 20.56 | 30.7 | 27 | 41.11 |
| Propanol selectivity | 21.56 | 33.6 | 31.6 | 19.82 |
| 1-butanol selectivity | 5.37 | 2 | 5 | 4 |
| Selectivity for higher alcohols | 9.16 | 3.8 | 2.5 | 0.82 |
| Selectivity total alcohols | 67.26 | 96.31 | 90.2 | 84.00 |
| Selectivity C2&C3 alcohol | 42.12 | 64.3 | 58.6 | 60.93 |
| Yield C2&C3 alcohol | 17.27 | 18.00 | 20.51 | 25.59 |

Table 1 clearly shows that the catalyst produced by the method of the present invention has a significantly increased selectivity for alcohols when compared to a conventional carbon supported cobalt molybdenum catalyst or when compared to a carbon supported cobalt molybdenum catalyst wherein the soluble cobalt-comprising compound and the soluble molybdenum-compound are dissolved in water. Also the yield (conversion*fraction of selectivity) of C2 and C3 alcohol can be significantly increased by using the catalyst of the present invention. In addition thereto, a dramatic decrease in $CO_2$ formation could be observed, which is an undesired side-product produced in F-T synthesis.

The invention claimed is:

1. Method for preparing a catalyst composition comprising cobalt (Co) and molybdenum (Mo) on an activated carbon support comprising the steps:
   (a) dissolving a soluble cobalt-comprising compound and a soluble molybdenum-compound in one or more organic solvents that are miscible with water to form a cobalt- and molybdenum-comprising solution;
   (b) admixing an aqueous alkaline solution to the cobalt- and molybdenum-comprising solution in the presence of activated carbon support to precipitate an insoluble cobalt- and molybdenum-comprising compound on the activated carbon support to form a solid catalyst precursor; and
   (c) separating the solid catalyst precursor from the liquids, washing and drying the solid catalyst precursor and calcining the solid catalyst precursor in an inert atmosphere.

2. The method according to claim 1, wherein in step (a) the soluble cobalt-comprising compound and the soluble molybdenum-compound are separately dissolved in one or more organic solvents that are miscible with water followed by admixing the cobalt-comprising solution and the molybdenum-comprising solution to form the cobalt- and molybdenum-comprising solution.

3. The method according to claim 2, wherein the organic solvent that is miscible with water wherein the cobalt-comprising compound is dissolved and the organic solvent that is miscible with water wherein the molybdenum-comprising compound is dissolved are different.

4. The method according to claim 1, wherein the one or more organic solvents that are miscible with water are selected from the group consisting of methanol, ethanol, 1-butanol, propanol, pentanol, hexanol, ethylene glycol and glycerol.

5. The method according to claim 1, wherein the alkaline solution is selected from the group consisting of aqueous ammonia, sodium carbonate, ammonium bicarbonate and ammonium carbonate.

6. The method according to claim 1, wherein the activated carbon support is selected from the group consisting of activated carbon derived from coconut shell, peat, wood and synthetic carbon nano tubes.

7. The method according to claim 1, wherein the solid catalyst precursor is calcined at about 350-650° C. for about 3-8 hrs.

8. The method according to claim 1, wherein the inert atmosphere is selected from the group consisting of helium, argon and nitrogen.

9. The method according to claim 1, wherein the cobalt- and molybdenum-comprising solution and the alkaline solution are heated to about 60-95° C., preferably to about 70-90° C. and most preferably to about 75-85° C. before admixing in step (c) to form the solid catalyst precursor.

* * * * *